US011064732B2

(12) United States Patent
Cyphert et al.

(10) Patent No.: US 11,064,732 B2
(45) Date of Patent: Jul. 20, 2021

(54) ELECTRONIC VAPORIZER CARTRIDGE WITH ENCASED HEAT SOURCE

(71) Applicant: Healthier Choices Management Corp, Hollywood, FL (US)

(72) Inventors: Gilbert Cyphert, Phoenix, AZ (US); Edwin Balder, Mesa, AZ (US); Daniel Julia, Phoenix, AZ (US); Jeffrey E. Holman, Hollywood, AZ (US)

(73) Assignee: Healthier Choices Management Corp., Hollywood, FL (US)

( * ) Notice: Subject to any disclaimer, the term of this patent is extended or adjusted under 35 U.S.C. 154(b) by 149 days.

(21) Appl. No.: 16/218,853

(22) Filed: Dec. 13, 2018

(65) Prior Publication Data

US 2019/0124975 A1 May 2, 2019

Related U.S. Application Data

(63) Continuation-in-part of application No. 15/786,364, filed on Oct. 17, 2017, now abandoned, which is a continuation-in-part of application No. 15/298,147, filed on Oct. 19, 2016, now abandoned, which is a continuation of application No. 13/999,652, filed on Mar. 14, 2014, now Pat. No. 9,538,788.

(60) Provisional application No. 61/852,336, filed on Mar. 15, 2013.

(51) Int. Cl.
*A24F 7/04* (2006.01)
*A61M 15/06* (2006.01)
*A61M 11/04* (2006.01)
*A24D 3/10* (2006.01)
*A24F 40/46* (2020.01)
*A24F 40/485* (2020.01)

(52) U.S. Cl.
CPC .................. *A24F 7/04* (2013.01); *A24D 3/10* (2013.01); *A24F 40/46* (2020.01); *A24F 40/485* (2020.01); *A61M 11/042* (2014.02); *A61M 15/06* (2013.01); *A61M 2205/3653* (2013.01); *A61M 2205/75* (2013.01); *A61M 2205/8206* (2013.01)

(58) Field of Classification Search
None
See application file for complete search history.

(56) References Cited

U.S. PATENT DOCUMENTS 3,211,826 A * 10/1965 Holcomb .............. C03C 27/044
174/50.64
3,721,852 A * 3/1973 Chiola ...................... H01J 9/28
174/50.64
3,991,337 A * 11/1976 Notelteirs ................. H01J 5/38
174/50.61

(Continued)

*Primary Examiner* — Thor S Campbell
(74) *Attorney, Agent, or Firm* — Berger Singerman LLP; Geoffrey Lottenberg

(57) ABSTRACT

A cartridge for an electronic smoking device includes a heat source comprising a bulb-encased heating element. The heat source is disposed inside a compartment of the cartridge. The compartment extends from an air flow tube. The housing includes a storage area for retaining inhalant material. The cartridge includes a threaded connector that attaches to a control unit that has a power supply such as a batter. The cartridge avoids direct contact between the inhalant material and any metal components of the cartridge by either eliminating metal components or by encasing the metal components in glass, quartz, or ceramic.

11 Claims, 2 Drawing Sheets

(56) References Cited

U.S. PATENT DOCUMENTS

| | | | | | |
|---|---|---|---|---|---|
| 4,307,318 | A * | 12/1981 | Nixon | | H01K 1/18 |
| | | | | | 313/315 |
| 4,539,509 | A * | 9/1985 | Varshneya | | H01K 1/38 |
| | | | | | 313/315 |
| 4,756,701 | A * | 7/1988 | Danko | | H01K 1/28 |
| | | | | | 313/569 |
| 4,766,346 | A * | 8/1988 | Weiss | | H01K 1/38 |
| | | | | | 313/579 |
| 5,144,201 | A * | 9/1992 | Graham | | H01J 61/547 |
| | | | | | 313/634 |
| 5,913,705 | A * | 6/1999 | Kiesel | | H01J 9/247 |
| | | | | | 445/27 |
| 6,424,089 | B1 * | 7/2002 | Binder | | H01K 1/325 |
| | | | | | 313/634 |
| 7,358,674 | B2 * | 4/2008 | Bewlay | | C23C 30/00 |
| | | | | | 313/623 |
| 7,965,026 | B2 * | 6/2011 | Aurongzeb | | H01K 1/28 |
| | | | | | 313/345 |
| 8,277,274 | B2 * | 10/2012 | Emilsson | | H01J 61/368 |
| | | | | | 445/58 |
| 8,729,801 | B2 * | 5/2014 | Fransson | | H01J 61/33 |
| | | | | | 313/634 |
| 9,004,073 | B2 * | 4/2015 | Tucker | | A24F 40/70 |
| | | | | | 131/273 |
| 9,427,022 | B2 * | 8/2016 | Levin | | A24F 47/008 |
| 10,653,186 | B2 * | 5/2020 | Verleur | | A61M 11/042 |
| 2008/0092912 | A1 * | 4/2008 | Robinson | | A24B 3/14 |
| | | | | | 131/200 |
| 2010/0314655 | A1 * | 12/2010 | Thompson | | H05K 1/189 |
| | | | | | 257/99 |
| 2011/0036346 | A1 * | 2/2011 | Cohen | | A24F 47/008 |
| | | | | | 128/200.14 |
| 2011/0094523 | A1 * | 4/2011 | Thorens | | H05B 1/0202 |
| | | | | | 131/194 |
| 2012/0111347 | A1 * | 5/2012 | Hon | | A61M 11/042 |
| | | | | | 131/329 |
| 2012/0174914 | A1 * | 7/2012 | Pirshafiey | | A61M 11/041 |
| | | | | | 128/200.14 |
| 2012/0199663 | A1 * | 8/2012 | Qiu | | A61M 15/0081 |
| | | | | | 239/8 |
| 2013/0213419 | A1 * | 8/2013 | Tucker | | H05B 3/141 |
| | | | | | 131/328 |
| 2013/0220315 | A1 * | 8/2013 | Conley | | H05B 1/0244 |
| | | | | | 128/202.21 |
| 2013/0228191 | A1 * | 9/2013 | Newton | | A24F 47/008 |
| | | | | | 131/329 |
| 2013/0298905 | A1 * | 11/2013 | Levin | | A24F 47/008 |
| | | | | | 128/202.21 |
| 2013/0319407 | A1 * | 12/2013 | Liu | | A61M 11/044 |
| | | | | | 128/202.21 |
| 2015/0305409 | A1 * | 10/2015 | Verleur | | H02J 7/0042 |
| | | | | | 131/329 |

* cited by examiner

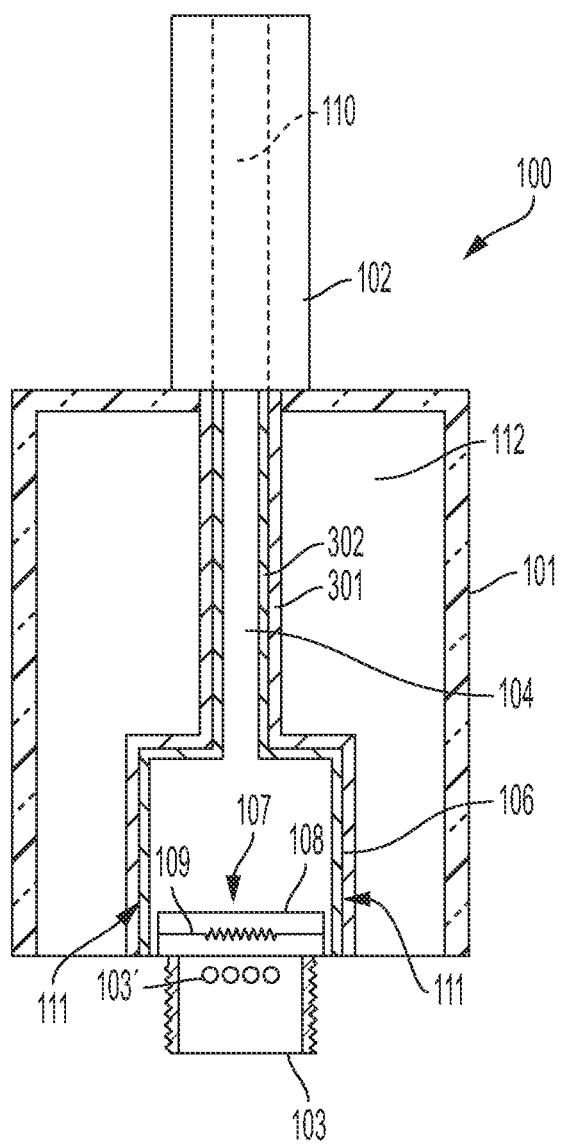
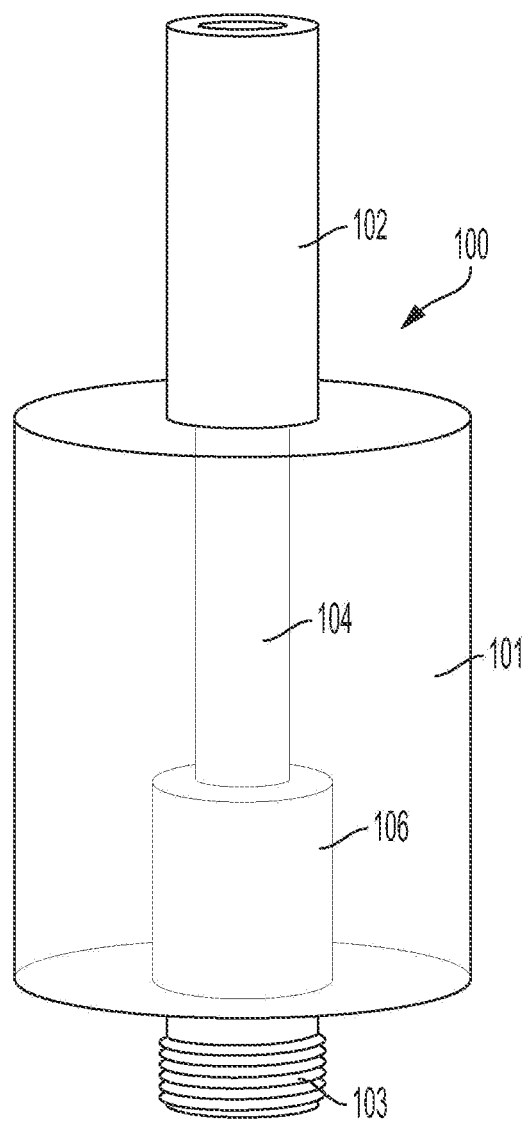
FIG. 1A
FIG. 1B

ELECTRONIC VAPORIZER CARTRIDGE WITH ENCASED HEAT SOURCE

CROSS REFERENCE TO RELATED APPLICATIONS

This application is a continuation-in-part of U.S. application Ser. No. 15/786,364 filed Oct. 17, 2017, which is a continuation-in-part of U.S. application Ser. No. 15/298,147 filed Oct. 19, 2016, which is a continuation of U.S. application Ser. No. 13/999,652 filed Mar. 14, 2014, now U.S. Pat. No. 9,538,788, which claims priority to U.S. Provisional Application No. Ser. No. 61/852,336, filed Mar. 15, 2013.

FIELD OF THE INVENTION

The present invention relates to electronic cigarettes and vaporizers.

BACKGROUND OF THE INVENTION

In an attempt to solve the problems of traditional smoking, electronic cigarettes and vaporizers have come to the forefront. These devices employ the use of a liquid, concentrate, or dry material inhalants that often comprise glycol ad-mixtures, wax-like substances, herbs, flowers, and other medicinal substances. In the conventional art, the inhalant is placed on or otherwise drawn to and over a metal heating element, such as a metal coil, which coil receives electrical energy from an on-board battery. The electrical energy is converted to heat, thereby heating and vaporizing the inhalant material brought in contact with the heating element. The resultant vapor, smoke, or other aerosol is then inhaled by way of a mouthpiece in fluid communication with an air channel disposed through the device.

In most electronic cigarettes and vaporizers, the inhalant material is brought into direct contact with a metal heat source such as a heating element or conductive tube, which heats and often burns or combusts the inhalant material through conduction. The downside of these electronic cigarette and vaporizer systems is that repeated heating and cooling of the metal heat source will cause transfer of heavy metals into the resultant vapor or smoke, resulting in inhalation of harmful and unwanted heavy metal material. Recent studies have in fact shown that heavy metal exposure caused by traditional electronic cigarettes and vaporizers is as harmful as or possibly more harmful than exposure to the carcinogens found in traditional cigarettes.

In addition to the toxicity issues associated with direct contact between the target inhalant material and the metal heat source, traditional electronic cigarette and vaporizer systems suffer from degradation of and eventual loss of performance due to waste buildup on the metal heat source and the surrounding area. As the buildup continues to develop, the device tends to generate less available smoke or vapor and the flavor and "hit" consistency will be impacted. Sooner than later the metal heat source will need to be cleaned using toxic chemicals or, in most cases, will need to be replaced regularly.

Accordingly, the present invention is directed at an alternative and improved vaporizer cartridge to be used with electronic cigarettes and vaporizer systems. Namely, the present invention contemplates various embodiments of a vaporizer cartridge having an encased heat source that limits and in many cases prevents direct contact between the inhalant material and the metal heat source.

BRIEF DESCRIPTION OF THE DRAWINGS

FIG. 1A is a cutaway view of one embodiment of the vaporizer cartridge.

FIG. 1B is a perspective view of the vaporizer cartridge shown in FIG. 1A.

Figure 2A:
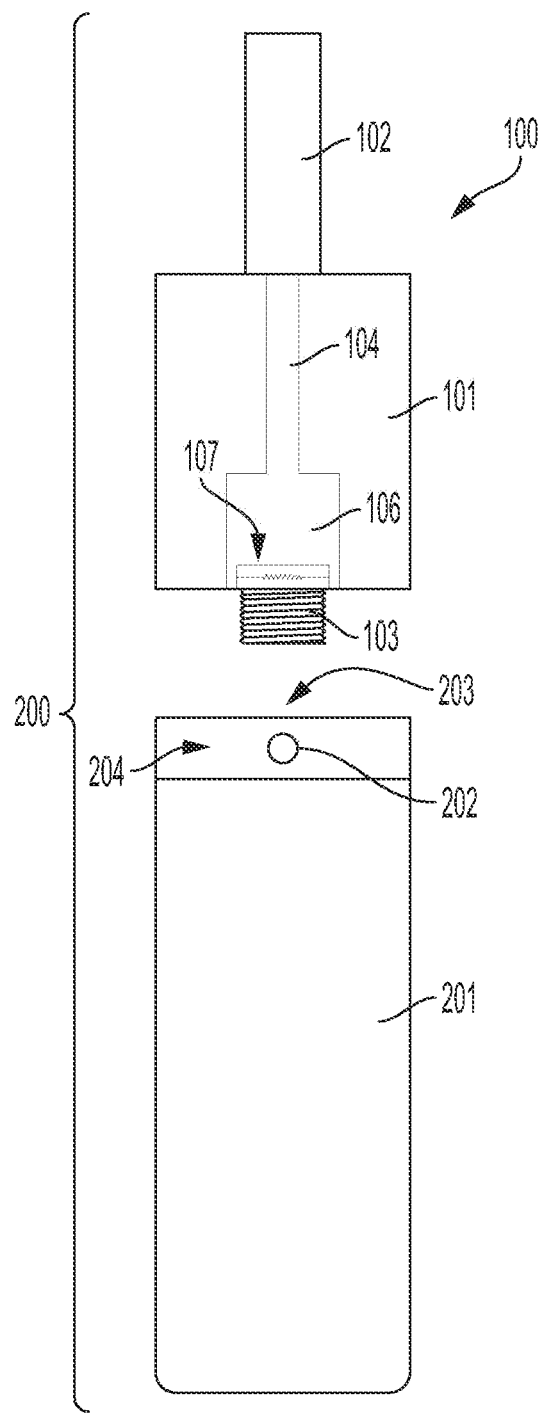
FIG. 2A is an exploded view showing the heating device shown in FIGS. 1A-1B in use with an electronic smoking device.

It will be recognized that some or all of the Figures are schematic representations for purposes of illustration and do not necessarily depict the actual relative sizes or locations of the elements shown. The Figures are provided for the purpose of illustrating one or more embodiments of the invention with the explicit understanding that they will not be used to limit the scope or the meaning of the claims.

DETAILED DESCRIPTION

In the following description, for the purposes of explanation, numerous specific details are set forth in order to provide a thorough understanding of the present invention. It will be apparent, however, to one skilled in the art that the present invention may be practiced without some of these specific details. Throughout this description, the embodiments and examples shown should be considered as exemplars, rather than as limitations. That is, the following description provides examples, and the accompanying drawings show various examples for the purposes of illustration. However, these examples should not be construed in a limiting sense as they are merely intended to provide examples of the present invention rather than to provide an exhaustive list of all possible implementations.

Specific embodiments of the invention will now be further described by the following, non-limiting examples which will serve to illustrate various features. The examples are intended merely to facilitate an understanding of ways in which the invention may be practiced and to further enable those of skill in the art to practice the invention. Accordingly, the examples should not be construed as limiting the scope of the invention. In addition, reference throughout this specification to "some embodiments" or "one embodiment" or "an embodiment" means that a particular feature, structure or characteristic described in connection with the embodiment is included in at least one embodiment of the present invention. Thus, appearances of the phrases "in some embodiments" or "in an embodiment" in various places throughout this specification are not necessarily all referring to the same embodiment. Furthermore, the particular features, structures or characteristics may be combined in any suitable manner in one or more embodiments.

For purposes of this disclosure, the terms "electronic cigarette" and "vaporizer" are interchangeable and generally refer to an electronic device configured to heat a target inhalant material to be inhaled by the user by mouth. "Inhalant material" for purposes of this disclosure refers to any desired material to be heated and inhaled by way of the electronic cigarette or vaporizer. Such materials include, without limitation, liquids such as glycol-based solutions, semi-solid or solid concentrates such as oils and waxes, shatter, and dry material such as tobacco, herbs, flowers, and aromatics. The term "vaping" refers generally to the act of using electronic cigarettes and vaporizers for the purposes of generating vapor, smoke, aerosol or other material to be inhaled for pleasure or for the delivery of medicaments or substances to the body; notably, the term is not limited to the act of generating or inhaling only vapor—it refers more broadly to the act of inhaling material by way of electronic devices, as opposed to traditional smoking implements such as cigarettes, pipes, cigars, and the like.

With reference to FIGS. 1A-1B shown is an embodiment of a vaporizer cartridge 100 configured as a modular device intended to be attached to a power source such as a battery. In some embodiments, the cartridge 100 comprises a housing 101, a mouthpiece 102, and a connector element 103. In some embodiments, the housing comprises a generally cylindrical element configured to store inhalant material and provide the heat source needed to heat same for inhalation. Although shown as generally cylindrical, other shapes may be equally suitable for housing 101. The mouthpiece 102 extends upward from the top of the housing 101 and may be integrated or removable from the housing 101. Extending from the bottom of the housing 101 is a connector element 103 which, in some embodiments, comprises a threaded connector to provide a physical and electrical connection to a power source as further described herein. The connector element 103 includes one or more apertures 103' which permit the introduction of air flow through the cartridge.

Disposed inside the housing 101 is a central air flow tube 104 which is in flow communication with an air passageway 110 of the mouthpiece 102 and the apertures 103' at the connector element. Disposed between the air flow tube 104 and the housing 101 is an internal storage area 112 wherein inhalant material is stored and retained. Toward the bottom of the air flow tube 104 and extending therefrom is flanged compartment 106. Disposed inside the compartment 106 is a heat source 107. In some embodiments, the heat source 107 comprises a heating element 109 encased inside a bulb 108, the bulb comprising glass, quartz, ceramic, or other silica-containing compositions. Such a heat source 107 is described in detail in Applicant's U.S. patent application Ser. Nos. 13/999,652; 15/786,364; 15/796,618; and 15/917,453 each of which is hereby incorporated by reference in its entirety. The compartment 106 includes one or more apertures 111 which introduce inhalant material from the internal storage area 112 into the compartment 106 so that it can be heated by the heat source 107. The heat source 107 is electrically coupled to the connector element 103, which connector element 103 is connected to a power source as further described herein.

Figure 2B:
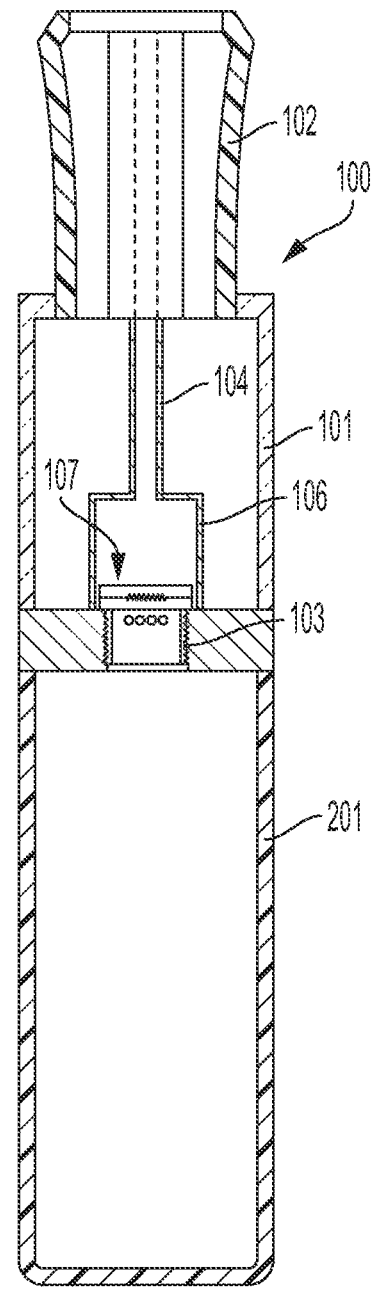
FIG. 2B is a cutaway assembled view showing the heating device shown in FIGS. 1A-1B in use with an electronic smoking device.

With reference to FIGS. 2A and 2B, shown is the cartridge 100 in use with an exemplary electronic smoking device 200. The configuration smoking device 200 is for exemplary purposes only, but in this case comprises a modular type vaporizer that includes a control section 201 and heating device 100. The control section 201 comprises a battery or other power supply and chipset to control the device 200. In some embodiments, the cartridge 100 is removably and threadingly engaged at the lower connector 103 with the attachment point 203 of the control section 201 to provide a physical and electrical connection between the heating device 100 and the battery or power supply of the control unit 201. In some embodiments, the control section 201 has a an internally or female threaded attachment point 203 that engages the externally or male threaded connector 103 of the cartridge 100. In some embodiments, the control section 201 include external apertures 204 and air passages to allow for the passage of air through the cartridge 100 in order to draw vapor, smoke, or aerosol there-through. Accordingly in some embodiments an air passageway is defined from the control section 201, through the apertures 103' of the connector 103, through the air flow tube 104 and out of the air passage 110 at the mouthpiece 102.

The electronic smoking device 200 is assembled first by threading the cartridge 100 onto the control unit 201. In some embodiments the control unit 201 includes a battery or other power supply such that when the control unit 201 is connected to the cartridge 100, an electrical connection is established between the control until 201 and the heat source 107 of the cartridge 100. In use, the inhalant material is provided into the internal storage area 112, it can either be pre-loaded or loaded by the user on demand. Then the user activates the electronic smoking device 200, typically by a control button 202, which applies electric current to the heating element 109 of the heat source 107. As the user inhales through the mouthpiece 102, inhalant material is drawn into the compartment 106 through apertures 111 and toward the heat source 107. In some embodiments, the inhalant material comes into close proximity or in contact with the bulb 108 of the heat source 107. Heat generated by the heating element 109 heats the bulb 108 which in turn heats the inhalant material. The inhalant material then turns into a vapor, smoke, or aerosol to be inhaled by the user through air passage within the device and out of the mouthpiece 102. In some embodiments, air passes through the electronic smoking device 200 components and through the air passage 110 of the heating device 100 such that the vapor, smoke, or aerosol is released and pulled out of the cartridge 100 through the mouthpiece 102.

Recognizing that in the present invention it is advantageous to limit and/or prevent direct contact between the inhalant material and any metal components of the cartridge 100, in some embodiments at least the housing 101, air flow tube 104, compartment 106, and bulb 108 (as previously mentioned) are comprised of an inert and stable non-metallic material such as glass, quartz, ceramic, or other silica containing compositions. In other embodiments, the air flow tube 104 and compartment 106 are comprised of a metal 302 encased at least partially in an inert material 301 such as glass, quartz, ceramic, or other silica containing compositions. For example, air flow tube 104 could comprise a metal tube core 302 surrounded by a concentrically disposed quartz encasement 301 on either or both sides thereof. The selection of an encased heat source 107, such as a heating element 109 encased in a quartz bulb 108, enhances the safety and usability of the heating device by preventing direct contact between the inhalant material and the heating wire of the heating element that can result in a toxic reaction and buildup of residue on the heating device components. The avoidance of direct contact between the inhalant material and the heating element also has the further advantage of improving flavor and vapor (or smoke or aerosol) concentration as it provides a cleaner reaction. Any of these heating elements 109 can be implemented into the heating devices described herein to initiate a heating, vaporization (phase change), or combustion reaction inside the device.

It is appreciated that the present invention provides a substantial improvement to traditional vaporizer cartridges by significantly limiting or even preventing direct contact between the inhalant material and any metal components such as the heating element 109 or otherwise. This limiting of direct contact provides safety and convenience benefits in that a toxic reaction is limited or avoided, and the cartridge 100 will tend to accumulate less residue than other systems. Additionally, the configuration reduces a wasteful toxic reaction which can improve heating consistency and speed and can more thoroughly and completely heat and exhaust a given portion of inhalant material. The configuration also has the further advantage of improving flavor and vapor (or smoke or aerosol) concentration as it provides a cleaner heating process given the cumulative effects of these advantages.

As discussed herein, the various connector elements of the embodiments of the heating devices can, in some embodiments, function to provide both a physical connection between components and an electrical connection between components. In some embodiments, the connectors are configured with the aforementioned electrical contacts and/or anode/cathode configuration that interconnect and electrically couple the anode/cathode of the heating element to the anode/cathode of the battery or other power supply. In some embodiments, such as those shown herein, at least one or more of the connectors is threaded. However, the present invention is not limited to threaded connectors as other physical connections means are equally suitable such as interference fits, snap-fits, spring-biased fits, magnetic connections, and combinations thereof and the like.

It is to be noticed that the term "comprising," used in the claims, should not be interpreted as being limitative to the means listed thereafter. Thus, the scope of the expression "a device comprising means A and B" should not be limited to devices consisting only of components A and B. It means that with respect to the present invention, the only relevant components of the device are A and B. Put differently, the terms "including", "comprising" and variations thereof mean "including but not limited to", unless expressly specified otherwise. Similarly, it is to be noticed that the term "coupled", also used in the claims, should not be interpreted as being limitative to direct connections only. Thus, the scope of the expression "a device A coupled to a device B" should not be limited to devices or systems wherein an output of device A is directly connected to an input of device B. It means that there exists a path between an output of A and an input of B which may be a path including other devices or means. The enumerated listing of items does not imply that any or all of the items are mutually exclusive, unless expressly specified otherwise. The terms "a", "an" and "the" mean "one or more", unless expressly specified otherwise. Elements of the invention that are in communication with each other need not be in continuous communication with each other, unless expressly specified otherwise. In addition, elements of the invention that are in communication with each other may communicate directly or indirectly through one or more other elements or other intermediaries.

One skilled in the art will appreciate that the present invention can be practiced by other than the above-described embodiments, which are presented in this description for purposes of illustration and not of limitation. The specification and drawings are not intended to limit the exclusionary scope of this patent document. It is noted that various equivalents for the particular embodiments discussed in this description may practice the invention as well. That is, while the present invention has been described in conjunction with specific embodiments, it is evident that many alternatives, modifications, permutations and variations will become apparent to those of ordinary skill in the art in light of the foregoing description. Accordingly, it is intended that the present invention embrace all such alternatives, modifications and variations as fall within the scope of the appended claims. The fact that a product, process or method exhibits differences from one or more of the above-described exemplary embodiments does not mean that the product or process is outside the scope (literal scope and/or other legally-recognized scope) of the following claims.

What is claimed, is:

1. A cartridge for an electronic smoking device, comprising:
    a housing, a mouthpiece, and a connector element, the mouthpiece extending upward from a top of the housing and the connector element extending from a bottom of the housing;
    an air flow tube disposed in the housing and defining an air flow passageway through the housing, the air flow tube comprising quartz-encased metal;
    an internal storage area disposed between the airflow tube and the housing, wherein the internal storage area is configured to retain inhalant material;
    a compartment extending from the air flow tube, the compartment containing a heat source, the heat source comprising a metal heating element encased inside a bulb; and
    wherein the heat source is electrically coupled to the connector element, wherein the connector element is configured to transmit electrical current from a power source to the heat source.

2. The cartridge of claim 1, wherein the housing comprises glass, quartz, or ceramic.

3. The cartridge of claim 1, wherein the bulb comprises glass, quartz, or ceramic.

4. The cartridge of claim 1, wherein the air flow tube comprises a metal tube core surrounded by a concentrically disposed quartz encasement.

5. The cartridge of claim 1, wherein the connector element includes one or more apertures in air flow communication with the air flow passageway.

6. The cartridge of claim 1, wherein the mouthpiece is in air flow communication with the air flow passageway.

7. An electronic smoking device, comprising:
    a cartridge and a control section;
    the control unit comprising a power supply and an attachment point;
    the cartridge comprising:
        a housing, a mouthpiece, and a connector element, the mouthpiece extending upward from a top of the housing and the connector element extending from a bottom of the housing;
        an air flow tube disposed in the housing and defining an air flow passageway through the housing, the air flow tube comprising quartz-encased metal;
        an internal storage area disposed between the airflow tube and the housing, wherein the internal storage area is configured to retain inhalant material;
        a compartment extending from the air flow tube, the compartment containing a heat source, the heat source comprising a heating element encased inside a bulb; and
        the heat source electrically coupled to the connector element,
    wherein the connector element of the cartridge is removably connected to the attachment point of the control unit such that the power supply of the control unit transmits electrical current to the heat source through the connector element.

8. The electronic smoking device of claim 7, wherein the housing comprises glass, quartz, or ceramic.

9. The electronic smoking device of claim 7, wherein the bulb comprises glass, quartz, or ceramic.

10. The electronic smoking device of claim 7, wherein the air flow tube comprises a metal tube core surrounded by a concentrically disposed quartz encasement.

11. A cartridge for an electronic smoking device, comprising:
- a housing, a mouthpiece, and a connector element, the mouthpiece extending upward from a top of the housing and the connector element extending from a bottom of the housing;
- an air flow tube disposed in the housing and defining an air flow passageway through the housing, the air flow tube comprising quartz-encased metal;
- an internal storage area disposed between the airflow tube and the housing, wherein the internal storage area is configured to retain inhalant material;
- a compartment extending from the air flow tube, the compartment containing a heat source, the heat source comprising a heating element encased inside a bulb;
- wherein the heat source is electrically coupled to the connector element, wherein the connector element is configured to transmit electrical current from a power source to the heat source;
- and wherein at least one of the housing, air flow tube, and bulb comprising glass, quartz, or ceramic.

* * * * *